United States Patent [19]

Monte et al.

[11] 4,122,062
[45] Oct. 24, 1978

[54] ALKOXY TITANATE SALTS USEFUL AS COUPLING AGENTS

[75] Inventors: Salvatore J. Monte, Staten Island, N.Y.; Gerald Sugerman, Allendale, N.J.

[73] Assignee: Kenrich Petrochemicals, Inc., Bayonne, N.J.

[21] Appl. No.: 618,224

[22] Filed: Sep. 30, 1975

Related U.S. Application Data

[63] Continuation-in-part of Ser. No. 577,922, May 15, 1975.

[51] Int. Cl.² ............................................. C08K 9/04
[52] U.S. Cl. ........................... 260/42.14; 106/299; 106/308 S; 260/40 R; 260/429.5; 428/403; 428/406
[58] Field of Search ............... 260/42.14, 40 R, 429.5; 428/403, 406; 106/299, 308 S, 308 Q

[56] References Cited

U.S. PATENT DOCUMENTS

| | | | |
|---|---|---|---|
| 3,337,391 | 8/1967 | Clayton et al. | 260/429.5 X |
| 3,617,333 | 11/1971 | Brown | 428/406 X |
| 3,660,134 | 5/1972 | Morris et al. | 106/299 X |
| 3,697,474 | 10/1972 | Morris et al. | 260/40 R |

FOREIGN PATENT DOCUMENTS 733,224 7/1955 United Kingdom.

OTHER PUBLICATIONS

Chemical Abstracts, par. 74:42016t. (Sep., 1970).

*Primary Examiner*—Sandra M. Person
*Attorney, Agent, or Firm*—Bert J. Lewen

[57] ABSTRACT

A composition of matter comprising organotitanates having one of the following formulas:

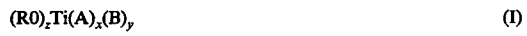

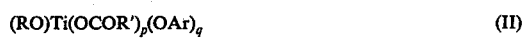

wherein R is a monovalent alkyl, alkenyl, alkynyl, or aralkyl group having from 1 to 30 carbon atoms or substituted derivatives thereof; A is a thioaroxy, sulfonyl, sulfinyl, diester pyrophosphate, diester phosphate, or a substituted derivative thereof; OAr is aroxy; B is OCOR' or OAr; R' is hydrogen or a monovalent organic group having from 1 to 100 carbon atoms; $x+y+z$ equal 4; $p+q$ equal 3; x, z and q may be 1, 2 or 3; and y and p may be 0, 1 or 2; the reaction products of such organo-titanates and comminuted inorganic material; and polymeric materials containing such reaction products.

47 Claims, No Drawings

ALKOXY TITANATE SALTS USEFUL AS COUPLING AGENTS

RELATED APPLICATION

This application is a continuation-in-part of U.S. patent application Ser. No. 577,922, filed May 15, 1975.

BACKGROUND OF THE INVENTION

Inorganic materials have long been used as fillers, pigments, reinforcements and chemical reactants in polymers. In general, these inorganic materials are hydrophilic, that is, easily wetted by water or able to absorb water, but their compatibility with organic polymers is limited. Because of this limited compatibility, the full potential of color, reinforcement, or chemical reactivity of the inorganic materials is not realized.

To overcome these difficulties, wetting agents have been used to minimize interfacial tension: but wetting agents, too, have serious deficiencies. In particular, relatively large proportions are necessary to produce adequate wetting of the finely divided inorganics. When used in large proportions, the wetting agents markedly detract from the properties of the finished composite. Coupling agents have been developed to overcome this difficulty. These fall into two main classes. The first, the more widely used, are trialkoxy organo functional silanes. Their activity is based upon chemical interaction between the alkoxy portion of the silane and filler and the chemical reaction of the organo functional portion with the polymer matrix. This provides a direct chemical link between the polymer and filler. But silanes have drawbacks. They are typically highly flammable, difficult to handle, and not easily worked into many polymer systems. Where the polymers do not contain functional groups or where the filler does not contain acidic protons, the silanes are often ineffective because of their inability to interact. For example, silanes are ineffective in thermoplastic hydrocarbons and fillers, such as carbon black, and to a large degree, calcium carbonate and sulfur.

The second group of coupling agents includes the organo-titanates which may be prepared by reacting tetraalkyl titanates with aliphatic or aromatic carboxylic acids. Of particular interest are the di- or trialkoxy acyl titanates or certain alkoxy triacyl titanates. These titanates, however, have serious drawbacks: e.g., they tend to decompose at temperatures frequently used in preparing many polymers; they tend to discolor certain inorganic materials used with polymer systems; and they are not compatible with many polymer systems.

DETAILS OF THE INVENTION

The subject invention relates to three novel alkoxy titanium salts and their uses. The first class may be represented by the following formula:

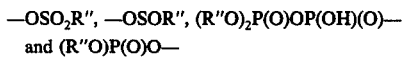

wherein R is a monovalent alkyl, alkenyl, alkynyl or aralkyl group having from 1 to about 30 carbon atoms or a substituted derivative thereof. The R group may be saturated or unsaturated, linear or branched, and may have from 1 to 6 substitutions including halogen, amino, epoxy, cyano, ether, thioether, carbonyl, aromatic nitro, or acetal. In a particular molecule, all of the R groups may be the same different, so long as they fall within the above class. It is preferred that the R group be alkyl having 1 to 6 carbon atoms and be all the same.

The monovalent group (A) may be thioaryloxy, sulfonic, sulfinic, diester pyrophosphate and diester phosphate. The thioaryloxy group may be a substituted or unsubstituted thiophenoxy or thionaphthyloxy group containing up to about 60 carbon atoms. It may be substituted by alkyl, alkenyl, aryl, aralkyl, alkaryl, halo, amino, epoxy, ether, thioether, ester, cyano, carbonyl, or aromatic nitro groups. Preferably no more than three substituents per aromatic ring are present. The thioaryloxy groups wherein the aryl is phenyl or naphthyl are preferred.

The sulfonic, sulfinic, diester pyrophosphate and diester phosphate ligand, respectively, are represented by the following formulas:

wherein R" may be the same as R' as defined below. Where A is a sulfonic or a sulfinic group, it is preferred that R" be phenyl, a substituted phenyl or an alkaryl group having from 5 to 24 carbon atoms in the alkyl chain. Where A is a phosphate group, it is preferred that the R" group have from 6 to 24 carbon atoms, and where A is a pyrophosphate group, it is preferred that the R" group be alkyl having up to 12 carbon atoms.

The monovalent group (B) may be acyloxy (OCOR') or aryloxy (OAr), R' may be hydrogen or a monovalent organic group having from 1 to about 100 carbon atoms; particularly, an alkyl, alkenyl, aryl, aralkyl or alkaryl group. The aryl groups may be substituted or unsubstituted phenyl or naphthyl groups, preferably containing up to 60 carbon atoms. Additionally, the R' group may be substituted with halo, amino, epoxy, ether, thioether, ester, cyano, carboxyl and/or aromatic nitro substituents. Generally up to about six substituents may occur per R' group. The R' group may contain intermediate hetero atoms such as sulfur or nitrogen in the main or pendant substituents. R' is preferably a long chain group having 18 carbon atoms. Most desirably, all R's are the same. In formula (I), the sum of $x$, $y$ and $z$ must be 4; $x$ and $z$ may be 1, 2 or 3; and $y$ may be 0, 1 or 2. Preferred are those compounds where $z = 1$.

The second class of compounds falling within the scope of the present invention may be represented by the following formula:

In the aforesaid formula, R and R' are as defined above; $p+q$ must be 3; $p$ may be 0, 1 or 2; and $q$ may be 1, 2 or 3 OAr is as defined above. These organo-titanate compounds having one or more of these long carbon chains are particularly effective for coupling agents used in connection with low density polyethylene. They increase the modulus of the products as well as their density.

A wide variety of ligands, subject to the limitations heretofore expressed, may be used in the practice of this invention. The most suitable depends upon the filler-polymer system and to a lesser degree upon the curative and/or extender systems employed.

Examples of specific R ligands are: methyl, propyl, cyclopropyl, cyclohexyl, tetraethyloctadecyl, 2,4-dichlorobenzyl, 1,-(3-bromo-4-nitro-7-acetylnaphthyl- )ethyl, 2-cyano-furyl, 3-thiomethyl-2-ethoxy-1-propyl and methallyl.

Examples of A ligands useful in the practice of this invention include 11-thiopropyl-12-phenyloctadecylsulfonic, 2-nitrophenylsulfinic, di-2-omega-chlorooctylphenyl phosphato, diisonicotinyl pyrophosphato, 2-nitro-3-iodo-4-fluorothiophenoxy, phenylsulfinic, 4-amino-2-bromo-7-naphthylsulfonic, diphenyl pyrophosphato, diethylhexyl pyrophosphato, di-sec-hexylphenyl phosphato, dilauryl phosphato, methylsulfonic, laurylsulfonic and 3-methoxynaphthalene sulfinic. Examples of B ligands are 2-methallylphenoxy, 3-cyano-4-methoxy-6-benzoylphenoxy and 2,4-dinitro-6-octyl-7-(2-bromo-3-ethoxyphenyl)-1-naphthyloxy.

Examples of the R' groups are numerous. These include straight chain, branched chain and cyclic alkyl groups such as hexyl, heptyl, octyl, decyl, dodecyl, tetradecyl, pentadecyl, hexadecyl, octadecyl, nonadecyl, eicosyl, docosyl, tetracosyl, cyclohexyl, cycloheptyl, and cyclooctyl. Alkenyl groups include hexenyl, octenyl and dodecenyl.

Halo-substituted groups include bromohexyl, chlorooctadecyl, iodotetradecyl and chlorooctadecenyl. One or more halogen atoms may be present, as for example in difluorohexyl or tetrabromooctyl. Ester-substituted aryl and alkyl groups include 4-carboxyethylcapryl and 3-carboxymethyltoluyl. Amino-substituted groups include aminocaproyl, aminostearyl, aminohexyl, aminolauryl and diaminooctyl.

In addition to the foregoing aliphatic groups, groups containing hetero-atoms, such as oxygen, sulfur or nitrogen, in the chain may also be used. Examples of these radicals are ethers of the alkoxyalkyl type, including methoxyhexyl and ethoxydecyl. Alkylthioalkyl groups include methylthiododecyl groups. Primary, secondary and tertiary amines may also serve as the terminal portion of the hydrophobic group. These include diisopropylamino, methylaminohexyl, and aminodecyl.

The aryl groups include the phenyl and naphthyl groups and substituted derivatives. Substituted alkyl derivatives include toluyl, xylyl, pseudocumyl, mesityl, isodurenyl, durenyl, pentamethylphenyl, ethylphenyl, n-propylphenyl, cumyl, 1,3,5-triethylphenyl, styryl, allylphenyl, diphenylmethyl, triphenylmethyl, tetraphenylmethyl, 1,3,5-triphenylphenyl. Nitro- and halo-substituted may be exemplified by chloronitrophenyl, chlorodinitrophenyl, dinitrotoluol, and trinitroxylyl.

Amine-substituted components include methylaminotoluyl, trimethylaminophenyl, diethylaminophenyl, aminomethylphenyl, diaminophenyl, ethoxyaminophenyl, chloroaminophenyl, bromoaminophenyl and phenylaminophenyl. Halo-substituted aryl groups include fluoro-, chloro-, bromo-, iodophenyl, chlorotoluyl, bromotoluyl, methoxybromophenyl, dimethylaminobromophenyl, trichlorophenyl, bromochlorophenyl, and bromoiodophenyl.

Groups derived from aromatic carboxylic acids are also useful. These include methylcarboxylphenyl, dimethylaminocarboxyltoluyl, laurylcarboxyltoluyl, nitrocarboxyltoluyl, and aminocarboxylphenyl. Groups derived from substituted alkyl esters and amides of benzoic acid may also be used. These include aminocarboxylphenyl and methoxycarboxyphenyl.

Titanates wherein R' is an epoxy group include tall oil epoxides (a mixture of 6 to 22 carbon alkyl groups) containing an average of one epoxy group per molecule and glycidol ethers of lauryl or stearyl alcohol.

Substituted naphthyl groups include nitronaphthyl, chloronaphthyl, aminonaphthyl and carboxynaphthyl groups.

Illustrative of the compounds of the instant invention are: $(i-C_3H_7O)Ti(OSOC_6H_4NH_2)_3$; $(i-C_3H_7O)Ti(OSO_2C_6H_4C_{12}H_{25})_2(OSO_2C_6H_4NH_2)$; $(i-C_3H_7O)Ti[OP(O)(OC_8H_{17})_2]_3$; $(i-C_3H_7O)Ti(OC_6H_4C(CH_3)_2C_6H_5)_3$; $(i-C_3H_7O)Ti[OP(O)(OC_{12}H_{25})]_3$; $(C_6H_{11}O)Ti(OC_6H_4NH_2)_3$; $(nC_4H_9O)_2Ti[OPO(OC_6H_4C_8H_{17})_2]_2$; $[C_6H_5O(CH_2)_3O]Ti[OCO(CH_2)_6(OSO_2)CH_3]_2$; $[CH_3O(CH_2)_2O]_2Ti(OCOC_6H_4Cl)[OP(O)(OH)OP(O)(OCH_3)_2]$; $(CH_3O)Ti(2-SC_{10}H_7)$ and $(i-C_3H_7O)(nC_{12}H_{25}O)Ti(OSO_2C_6H_5)_2$.

Another composition of matter of the invention comprises the reaction products of the aforesaid classes of alkoxy titanium salts with inorganic materials, especially when $x$ in the above formula is 3. The amount of the titanate reacted is at least 0.01 part, preferably from 0.1 to 5 parts, and most preferably between 0.2 and 2 parts, per 100 parts of inorganic solid. The optimum proportions required are a function of the inorganic solid and the alkoxy titanium salt selected, and the degree of the comminution, i.e., the effective surface area, of the inorganic solid. The reaction of the titanate takes place on the surface of the inorganic filler. The RO group splits off and an organic hydrophobic surface layer is formed on the inorganic solid. The unmodified inorganic solid is difficult to disperse in an organic medium because of its hydrophilic surface. The organo-titanium compound may be incorporated into an organic medium (low molecular weight liquids or higher molecular weight polymeric solids) with the inorganic solid. Alternatively, the organo-titanate may be first reacted with the inorganic solid in the absence of an organic medium and thereafter admixed with the latter.

By means of the present invention, the dispersion of inorganic materials in organic polymer media is improved and achieves (1) improved rheology or higher loading of the dispersate in the organic medium; (2) higher degrees of reinforcement by the use of fillers, thereby resulting in improved physical properties in the filled polymer; (3) more complete utilization of chemical reactivity, thereby reducing the quantity of inorganic reactive solids required; (4) more efficient use of pigments and opacifiers; (5) higher inorganic-to-organic ratios in a dispersion; and (6) shorter mixing times to achieve dispersion.

Also, according to the invention herein, the reaction with the RO groups may be carried out neat or in an organic medium to form a liquid, solid, or pastelike solid dispersion which can be used in the compounding of the final polymeric system. Such dispersions are very stable, i.e., having little tendency to settle, separate, or harden on storage to a non-dispersible state.

Moreover, the invention simplifies the making of inorganic dispersions in organic media by providing a means to eliminate the solvent, to reduce the cost of processing equipment, and to reduce the time and energy required to disperse an inorganic solid material in a liquid or polymeric organic solid.

The present invention results in the formation of a reinforced polymer which has a lower melt viscosity, improved physical properties, and better pigmenting characteristics than the prior art materials.

The practice of the present invention achieves a product comprising natural or synthetic polymers which contain particulate or fibrous inorganic materials which reinforce, pigment or chemically react with the polymer to produce a product having superior physical properties, better processing characteristics, and more efficient utilization of pigments.

Amongst the advantages gained by the practice of this embodiment of the present invention is the option of dispensing with the use of volatile and flammable solvents and the attendant need to dry the filler or to recover solvents. Furthermore, multi-molecular layer formation is minimized. Also, the dispersions of the present invention are non-oxidizing.

The inorganic materials may be particulate or fibrous and of varied shape or size, so long as the surfaces are reactive with the hydrolyzable groups of the organotitanium compound. Examples of inorganic reinforcing materials include metals, clay, carbon black, calcium carbonate, barium sulfate, silica, mica, glass and asbestos. Reactive inorganic materials include the metal oxides of zinc, magnesium, lead, and calcium and aluminum, iron filings and turnings, and sulfur. Examples of inorganic pigments include titanium dioxide, iron oxides, zinc chromate, ultramarine blues. As a practical matter, the particle size of the inorganic materials should not be greater than 1 mm, preferably from 0.1 micron to 500 micron.

It is imperative that the alkoxy titanium salt be properly admixed with the inorganic material to permit the surface of the latter to react sufficiently. The optimum amount of the alkoxy titanium salt to be used is dependent on the effect to be achieved, the available surface area of and the bonded water in the inorganic material.

Reaction is facilitated by admixing under the proper conditions. Optimum results depend on the properties of the alkoxy titanium salt, namely, whether it is a liquid or solid, and its decomposition and flash points. The particle size, the geometry of the particles, the specific gravity, the chemical composition, among other things, must be considered. Additionally, the treated inorganic material must be thoroughly admixed with the polymeric medium. The appropriate mixing conditions depend on the type of polymer, whether it is thermoplastic or thermosetting, its chemical structure, etc., as will be readily understood by those skilled in the art.

Where the inorganic material is pretreated with the organic titanate, it may be admixed in any convenient type of intensive mixer, such as a Henschel or Hobart mixer or a Waring blender. Even hand mixing may be employed. The optimum time and temperature are determined to obtain substantial reaction between the inorganic material and the organic titanate. Mixing is performed under conditions at which the organic titanate is in the liquid phase, at temperatures below the decomposition temperature. While it is desirable that the bulk of the hydrolyzable groups be reacted in this step, this is not essential where the materials are later admixed with a polymer, since the substantial completion of the reaction may take place in this latter mixing step.

Polymer processing, e.g., high shear mixing, is generally performed at a temperature well above the second order transition temperature of the polymer, desirably at a temperature where the polymer will have a low melt viscosity. For example, low density polyethylene is best processed at a temperature range of 170° to 230° C.; high density polyethylene from 200° to 245° C.; polystyrene from 230° to 260° C.; and polypropylene from 230° to 290° C. Temperatures for mixing other polymers are known to those skilled in the art and may be determined by reference to existing literature. A variety of mixing equipment may be used, e.g., two-roll mills, Banbury mixers, double concentric screws, counter or co-rotating twin screws and ZSK type of Werner and Pfaulder and Busse mixers.

When the organic titanate and the inorganic materials are dry-blended, thorough mixing and/or reaction is not readily achieved and the reaction may be substantially completed when the treated filler is admixed with the polymer. In this latter step, the organic titanate may also react with the polymeric material if one or more of the R' groups is reactive with the polymer.

The treated filler may be incorporated in any of the conventional polymeric materials, whether thermoplastic or thermosetting, whether rubber or plastic. The amount of filler depends on the particular polymeric material, the filler and the property requirements of the finished product. Broadly, from 10 to 500 parts of filler may be used per 100 parts of polymer, preferably from 20 to 250 parts. The optimum amount may be readily determined by one skilled in the art.

To illustrate further the invention, attention is directed to the following examples. In certain of these examples, the number of ligands per molecule is expressed for a mixed number. In such cases, it should be understood that the structural formula represents a blend of componds and the mixed number is the average number of such ligands in the blend.

Examples A to C describe the preparation of compounds within the scope of formulas (I) and (II) above.

EXAMPLE A: PREPARATION OF ISOOCTYL TRI(CUMYL PHENOXY) TITANIUM

To a pyrex-lined metal vessel, equipped with an agitator, internal heating and cooling means, a vapor condenser and a distillate trap, is added 1 mole of isooctanol, 3 moles of mixed isomer cumyl phenol and 2 liters of mixed isomer xylene. The reactor is stirred, flushed with nitrogen and 4.2 moles of sodamide are added at a controlled rate and with cooling to maintain the reaction mass at a temperature not over about 100° C. By-product ammonia is vented. The sodamide treatment forms a heavy slurry which is refluxed for about 10 minutes to remove dissolved ammonia. The reactor contents are then cooled to about 90° C. and maintained at this temperature while 1 mole of $TiCl_4$ is added over a period of three hours. After the $TiCl_4$ addition, the resulting mixture is refluxed for 2 hours, cooled to about 100° C. and filtered. The filter cake is washed with about 500 cc of xylene and discharged. The washings are combined with mother liquor and charged to a still. Volatiles are removed to give a bottoms having a boiling point at 10 mm Hg of over 150° C. weighing about 800 g. (This is over 95% of theory.) Elemental analysis of bottoms product, a heavy dark red paste or glossy solid, is consistent with the formula (i-$C_8H_{17}O)Ti[OC_6H_5C(CH_3)_2C_6H_5]_3$.

EXAMPLE B: PREPARATION OF $(CH_3O)_{0.6}Ti[OP(O)(OH)OP(O)(OC_8H_{17})_2]_{3.4}$

A reactor such as that described in Example A is charged with 1 mole of tetramethyl titanate. Thereafter, with stirring, 3.4 moles of dioctyl pyrophosphoric acid is added over about a one hour period. External cooling is maintained during the addition to maintain a reaction mass temperature in the 20° to 55° C. range. The reaction mixture formed is distilled to bottoms temperature of 150° C. to remove substantially all by-product methanol. Elemental analysis of the residual pale yellow heavy oil is consistent with the formula $(CH_3O)_{0.6}Ti[OP(O)(OH)OP(O)(OC_8H_{17})_2]_{3.4}$. The yield is over 95% of theory.

EXAMPLE C: PREPARATION OF $(o\text{-}ClC_6H_4CH_2O)_{1.2}Ti(OSO_2\ C_6H_4NH_2)_{2.8}$ In a reactor such as that described in Example A, a solution of 1 mole of tetraisopropyl titanate in 2 liters of 2,6-dimethylnaphthalene is heated at 200° C. While maintaining this temperature for a period of 2.5 hours, 1.25 moles of ortho-chlorobenzyl alcohol and 2.8 moles of mixed isomers of aminobenzene sulfonic acid are added sequentially. By-product volatiles (mainly methanol) are continuously removed by distillation. After cooling, the resulting grey solid is filtered, washed with cyclohexane and vacuum oven dried to give about 565 g (82% yield) of grey solid product. Said product is found to have an elemental analysis and OH number consistent with the above formula.

The following examples illustrate the use of the alkoxy titanium salts of the instant invention as coupling agents in inorganic-filled polymer systems. All parts are by weight unless otherwise indicated.

EXAMPLE 1 a master formulation was prepared containing 100 parts of chlorosulfonated chlorinated polyethylene (Hypalon 40, a trademark of E. I. duPont deNemours & Co., Inc.), 4 parts of finely divided magnesium oxide, 2 parts of low molecular weight polyethylene, 84 parts of calcium carbonate, 30 parts of a highly aromatic oil (Kenplast RD, a trademark of Kenrich Petrochemicals, Inc.), 3 parts of pentaerythritol 200, and 2 parts of an accelerator (Tetrone A, a trademark of E. I. duPont deNemours & Co., Inc.). Four formulations were tested. The first consisted of the foregoing formulation without more, and served as a control. To Formulations A, B and C, respectively, 1%, based on the filler, of the following compounds of the invention were added:

$(i\text{-}C_3H_7O)_{0.9}Ti(OSO_2C_6H_4C_{12}H_{25})_{3.1}$;
$(i\text{-}C_3H_7O)_{0.6}Ti[OPO(iC_8H_{17}O)_2]_{3.4}$; and
$(i\text{-}C_3H_7O)_{1.1}Ti(OSO_2C_6H_4C_{12}H_{25})_{1.7}(OSO_2C_6H_4NH_2)_{1.2}$.

All of the formulations were cured at 152° C. for 30 minutes. Table A shows the properties of the four compounds as originally tested and after oven aging for 7 days at 121° C.

TABLE A

|  | Formulation No. | | | |
| --- | --- | --- | --- | --- |
|  | Control | A | B | C |
| Original Properties at 24° C. | | | | |
| 200% Modulus, psi | 560 | 460 | 470 | 460 |
| 300% Modulus, psi | 670 | 540 | 560 | 540 |
| Tensile Strength, psi | 2170 | 2170 | 1840 | 1940 |
| Ultimate Elongation, percent | 540 | 550 | 530 | 530 |
| Shore A Hardness | 65 | 63 | 65 | 65 |
| Crescent Tear Resistance, #/In. (ASTM D624 - Die C) | 196 | 175 | 188 | 273 |
| Rheometer at 171° C., 3° Arc, 20' Motor, 100 Scale | | | | |
| ML-lb.-in. | 14.5 | 15.25 | 13 | 12.5 |
| MHF-lb.-in. | 49 | 55.5 | 53 | 50 |
| Ts-2, min. | 3.0 | 2.67 | 2.76 | 3.09 |
| Tc-90, min. | 14.25 | 16.73 | 18.17 | 18.23 |
| Oven Aged 7 Days at 121° C. | | | | |
| 200% Modulus, psi | 950 | 800 | 970 | 865 |
| 300% Modulus, psi | 1150 | 990 | 1270 | 1135 |

TABLE A-continued

|  | Formulation No. | | | |
| --- | --- | --- | --- | --- |
|  | Control | A | B | C |
| Tensile Strength, psi | 1770 | 1700 | 2000 | 1850 |
| Ultimate Elongation, percent | 420 | 435 | 410 | 425 |
| shore A Hardness | 73 | 73 | 72 | 73 |
| Hot Tear Resistance at 121° C., #/In. (ASTM D624 - Die C) | 183 | 153 | 186 | 233 |
| Percent Change on Aging | | | | |
| Tensile | −19.5 | −22 | +9 | −5 |
| Elongation | −22 | −21 | −23 | −20 |
| Tear Resistance | −7 | −13 | −1 | −15 |

The above data clearly show, among other things, that the formulations of the invention have a lower modulus than the control. Additionally, in the case of Formulation C, there is a marked improvement in tear resistance.

EXAMPLE 2

This example shows the utility of $(i\text{-}C_3H_7O)_{0.9}Ti(OSO_2C_6H_4C_{12}H_{25})_{3.1}$ for improving the properties of polyvinyl chloride plastisols. One hundred parts of a PVC resin (Geon 121, a trademark of B. F. Goodrich Chemical Co.), 100 parts of dioctylphthalate, 3 parts of a barium-cadmium stabilizer and 10 parts of calcium carbonate were prepared, to form a control. A second formulation was prepared, except that 10 parts of the calcium carbonate containing 1% (based on calcium carbonate) of the aforementioned organo-titanate compound are added in place of the unmodified calcium carbonate. Table B shows the viscosity at the time period indicated at 24° C. and the original properties of molded samples obtained after the 2 weeks of plastisol aging at 24° C. The molding was performed at 171° C.

TABLE B

|  | Formulation No. | |
| --- | --- | --- |
|  | Control | D |
| LTV Brookfield Viscosity at 21° C., #2 Spindle at 12 RPM | | |
| Initial | 1250 | 830 |
| 1 Week | 1637 | 1650 |
| 2 Weeks | 1650 | 1815 |
| Original Properties | | |
| 100% Modulus, psi | 520 | 440 |
| Tensile Strength, psi | 1890 | 1610 |
| Ultimte Elongation, % | 440 | 440 |
| Shore A Hardness | 67 | 64 |

In the case of Formulation D, it will be noted that there is a lower initial viscosity. This is an advantage for polyvinyl chloride plastisols, since low viscosity reduces the energy requirements for mixing. The reduced modulus and hardness of the product of Formulation D is of importance, since in the prior art it was necessary to use substantial amounts of plasticizer to achieve such properties. Furthermore, with plasticizer alone, it is not possible to reduce hardness and modulus, while holding the elongation constant.

EXAMPLE 3

This example shows the utility of the compounds of the invention in modifying the properties of a calcium carbonate-filled flexible polyvinyl chloride formulation. A control containing 100 parts of a PVC resin having a medium molecular weight, 1 part of a stabilizer (DS 207, a trademark of NL Industries), 67 parts of dioctyl phthalate, and 50 parts of finely divided calcium carbonate, was prepared. In addition, five other formulations were prepared having the same composition as the control, except that each was modified by hot blending at about 88° C. for 3 minutes in a blender with 0.5% by weight, based on the calcium carbonate, of the following compounds, respectively:

| Formulation No. | Organotitanate Compound |
|---|---|
| E | $(i\text{-}C_3H_7O)Ti(OSO_2C_6H_4C_{12}H_{25})_3$ |
| J | $(i\text{-}C_3H_7O)_{0.5}Ti[OP(O)(OC_8H_{17})_2]_{3.5}$ |

The following table shows the properties of the control and the formulations embodying the teachings of the invention:

TABLE C

| | Formulation No. | | |
|---|---|---|---|
| Original Properties | Control | E | J |
| Hardness, Shore A | 80 | 78 | 79 |
| Modulus, 100%, psi | 912 | 763 | 856 |
| Tensile, psi | 1790 | 1693 | 1750 |
| Ultimate Elongation, % | 300 | 310 | 340 |

The above data clearly show the advantages of the formulations of the invention. Formulations E and J show a reduced modulus and increased elongation without impairment of tensile strength.

EXAMPLE 4

To show the utility of the invention for modifying the properties of carbon black-filled styrene-butadiene copolymer rubber, four formulations were prepared. Two served as the control. The first, Control 1, contained 100 parts of styrene-butadiene polymer, 50 parts of HAF-type carbon black, 4 parts zinc oxide, 2 parts sulfur, 1 part of an accelerator (Santocure NS, a trademark of Monsanto Co.), 1 part of stearic acid, 10 parts of an aromatic extender oil and 2 parts of an antioxidant (Neozone A, a trademark of E. I. duPont deNemours & Co., Inc.). The second control was the same as the first, except that the carbon black was pretreated with 1% of $Ca(OCl)_2$ at 38° C. for 1 minute to improve receptivity of the carbon black to titanate coupling.

Formulations L and M were identical to Control 2, except that they also contained, respectively, 2 parts of $(i\text{-}C_3H_7O)_{0.8}Ti(OSO_2C_6H_4NH_2(_{3.2}$ and $(i\text{-}C_3H_7O)_{1.0}Ti(OC_6\text{-}H_4C(CH_3)_2C_6H_5(_{3.0}$.

Table D below shows the physical properties of the four formulations after being cured at 166° C. for 30 minutes.

TABLE D

| | Formulation No. | | | |
|---|---|---|---|---|
| Original Properties | Control 1 | Control 2 | L | M |
| 300% Modulus, psi | 1050 | 740 | 950 | 1660 |
| 400% Modulus, psi | 1450 | 1260 | 1420 | 2540 |
| Tensile, psi | 2500 | 2290 | 2920 | 2680 |
| Ultimate Elongation, percent | 550 | 560 | 620 | 420 |
| % Set at Break | 18 | 12 | 12 | 3 |

The advantages of the invention are shown by the above data. Note that Formulation L shows increases in both the elongation and the tensile strength, while Formulation M shows increased modulus and substantially reduced permanent set at break. This retention of dimensional stability at break is a particularly useful property for such applications as shock absorbers.

EXAMPLE 5

This example shows the compound of this invention in protecting mineral-filled polyethylene from attack by aqueous acid.

Two 1 × 3 × ⅛ inch test specimens of 50 weight percent magnesium silicate-filled high density polyethylene are injection molded in identical fashion, except that the magnesium silicate used in one is pretreated at about 38° C. with 1 wt. % of $(CH_3O)_{1.2}Ti(OSO_2C_6H_4C_{12}H_{25})_{2.8}$ for 1.5 minutes in an intensive mixer. The resulting specimens are then evaluated for acid etch resistance by placing a drop of 8% aqueous hydrochloric acid on each, covering with a petri dish and oven aging at 38° C. for 24 hours. Visual inspection of the aged test specimens shows that the untreated specimen has substantially more surface discoloration than has the treated one. Similar observations are made when the magnesium silicate is replaced by a like proportion anhydrous calcium sulfate.

EXAMPLE 6

This example teaches the use of compounds of this invention, viz., (T) $(i\text{-}C_3H_7O)_2Ti(OSO_2CH_2CH_2COCH=CH_2)_2$ and (U) $(BrCH_2CH_2O)Ti[(OP(O)(OCH_2CH=CH_2)_2]_3$ as flex property modifiers for polyester resin.

Formulations were prepared containing 100 parts of a cobalt activated polyester resin (GR 643, a trademark of W. R. Grace Co.), 1 part of methyl ethyl ketone peroxide, 60 parts of high surface area calcium carbonate, and 0.3 part of alkoxy titanium salt, as indicated in the Table below.

Samples measuring ½ × 5 × ⅛ inches thick were cast and cured at ambient temperature for 30 minutes. The castings were tested and the results shown in Table F below:

TABLE F

| Alkoxy Titanium Salt | Flex Modulus psi | Flexural Strength psi |
|---|---|---|
| None | $1.5 \times 10^6$ | $4 \times 10^3$ |
| T | $2.0 \times 10^6$ | $6 \times 10^3$ |
| U | $1.0 \times 10^6$ | $8 \times 10^3$ |

The above data establish clearly the improved flexural properties obtained by the use of the organotitanates of the invention.

In selecting the particular organo-titanate compound, the water content of the inorganic filler must be considered. If free or loosely bound water is present (e.g., water-washed clays, hydrated silica, alumina gel, magnesium silicate, talc, fiberglass, and aluminum silicate), the pyrophosphate coupling agents are particularly preferred. This is shown in the following examples.

EXAMPLE 7

A blend of 30 parts by weight of kaolin, non-calcined water-washed clay, and 70 parts of mineral oil was prepared. To portions of such blends were added 0.6 parts by weight of three of the organo-titanate compounds of the instant invention. Brookfield viscosities of the four dispersions are compared in Table G below.

Table G

| Alkoxy Titanium Salt | Brookfield Viscosity cps at 25° C. |
|---|---|
| None | 19,000 |
| Isopropyl triiosostearoyl titanate | 8,200 |
| Isopropyl tri(diisooctylphos- | |

| Alkoxy Titanium Salt | Brookfield Viscosity cps at 25° C. |
|---|---|
| phato)titanate | 5,200 |
| Isopropyl tri(dioctylpyrophosphato)titnate | 700 |

The above table clearly shows that each of the compounds of the instant invention reduces the viscosity of the clay-mineral oil dispersion. However, it will be noted that isopropyl tri(dioctylpyrophosphato)titanate gives unexpectedly superior viscosity reduction. This markedly lowers energy requirements for mixing.

EXAMPLE 8

The viscosity reduction of isopropyl tri(dioctylpyrophosphate)titanate is also effective with kaolin (non-calcined water-washed soft clay) dispersed in a chlorinated paraffin. To demonstrate this, a mixture containing 30 parts by weight of kaolin and 70 parts by weight of a chlorinated paraffin having a molecular weight of about 580 was prepared. The Brookfield viscosity was determined in the absence of the organo-titanate and with the addition of 0.3 part by weight. The test results showed the Brookfield viscosity, cps at 25° C., was reduced from 90,000 to 18,000 by the titanate addition.

EXAMPLE 9

This example shows the viscosity reduction of isopropyl tri(dioctylpyrophosphate)titanate on a dispersion of talc in a heavy mineral oil. The control contained 60% by weight of talc and 40% by weight of a heavy mineral oil (flash point ca. 105° C.). In the titanate-treated formulation, 1.8 parts of the aforesaid compound was dry-blended at 85° C. in a Waring blender with the talc (3% by weight based on talc). The control had a Brookfield viscosity at 25° C. of 26,500. In constrast, the formulation of the invention had a viscosity of only 11,000. Talc is another example of a filler having a high water content.

EXAMPLE 10

The effect of the organo-titanates of the instant invention on the impact strength of polyvinyl chloride (PVC) is shown in this example. The relative Gardner impact strength of a composition containing 100% rigid PVC was compared to a filled composition containing 40% of a fine grind calcium carbonate (particle size of 1 to 2 microns). Samples of the filled compositions were also admixed with varying amounts of the alkoxy titanate salts of the invention as specifically shown in Table H below. All of the tests in the table below show the filled composition with the exception of the first run, which is 100% rigid PVC.

Table H

| Alkoxy Titanate Salt | Pts. by/Wt./ 100 pts. of Filler | Relative Gardner Impact |
|---|---|---|
| None (100% PVC) | | 100 |
| None (Filled PVC) | | 12 |
| Isopropyl tri(dioctyl-phosphto) titanate | 0.4 | 51 |
|  | 1.2 | 79 |
| Isopropyl tri(dioctyl-pyrophosphato)titanate | 0.4 | 108 |
|  | 1.2 | 113 |

The above table clearly shows that the impact strength of the filled PVC is improved in each and every case by the addition of the titanates. Most striking is the improvement resulting from the addition of the pyrophosphate compound. Here the Gardner impact strength exceeds that of the 100% PVC composition.

Having thus described our invention, what we claim and desire to protect by Letters Patent is:

1. An organo-titanate having the formula $(RO)_z Ti(A)_x(B)_y$ wherein R is a monovalent alkyl, alkenyl, alkynyl, or aralkyl group having from 1 to 30 carbon atoms or substituted derivatives thereof; A is a thioaroxy, sulfinic, diester pyrophosphate, diester phosphate, or a substituted derivative thereof; B is OCOR' or aroxy; R' is hydrogen or a monovalent organic group having from 1 to 100 carbon atoms; $x + y + z = 4$; $x$ and $z$ may be 1, 2 or 3; and $y$ may be 0, 1 or 2.

2. The organo-titanate of claim 1 wherein R is an alkyl group containing from 1 to 6 carbon atoms.

3. The organo-titanate of claim 1 wherein A is a sulfinic group having the formula —OSOR''; and wherein R'' is a phenyl, a substituted phenyl or an alkaryl group having from 5 to 24 carbons in the alkyl chain, R is an alkyl group having from 1 to 6 carbon atoms, and $z$ equals 1.

4. The organo-titanate of claim 3 wherein R'' is an aminophenyl group and R is an isopropyl group.

5. The organo-titanate of claim 3 wherein R'' is a dodecylphenyl group and R is an isopropyl group.

6. The organo-titanate of claim 1 wherein A is a phosphate group having the formula $(R''O)_2P(O)O-$; R'' has from 6 to 24 carbon atoms; R is an alkyl group having from 1 to 6 carbon atoms; and $z$ equals 1.

7. The organo-titanate of claim 6 wherein R'' is an octyl group and R is an isopropyl group.

8. The organo-titanate of claim 1 wherein A is a pyrophosphate group having the formula $(R''O)_2P(O)OP(OH)O-$; and wherein R'' is an alkyl group having up to 12 carbon atoms, R is an alkyl group having from 1 to 6 carbon atoms, and $z$ equals 1.

9. The organo-titanate of claim 8 wherein R'' is an octyl group and R is an isopropyl group.

10. An organo-titanate having the formula $(RO)Ti(D)_3$ wherein R is a monovalent alkyl, alkenyl, alkynyl, or aralkyl group having from 1 to 30 carbon atoms or substituted derivatives thereof; and D is a sulfonic group or a substituted derivative thereof.

11. The organo-titanate of claim 10 wherein R is an alkyl group containing from 1 to 6 carbon atoms.

12. An organo-titanate having the formula $(RO)Ti(OCOR')_p(OAr)_q$ wherein R is a monovalent alkyl, alkenyl, alkynyl, or aralkyl group having from 1 to 30 carbon atoms or substituted derivatives thereof; OAr is aroxy; R' is hydrogen or a monovalent organic group having from 1 to 100 carbon atoms; $p + q = 3$; $q$ may be 1, 2 or 3; and $p$ may be 0, 1 or 2.

13. The organo-titanate of claim 12 wherein R is an alkyl group containing from 1 to 6 carbon atoms.

14. The organo-titanate of claim 12 wherein Ar is an alkyl-substituted derivative of a phenyl or a naphthyl group and R is an alkyl group having from 1 to 6 carbon atoms.

15. The organo-titanate of claim 12 wherein Ar is a cumylphenyl group and $q$ equals 3.

16. A composition of matter comprising a comminuted inorganic material reacted with an organo-titanate compound which may be represented by one of the following formulas:

wherein R is a monovalent alkyl, alkenyl, alkynyl, or aralkyl group having from 1 to 30 carbon atoms or substituted derivatives thereof; A is a thioaroxy, sulfonic, sulfinic diester pyrophosphate, diester phosphate, or a substituted derivative thereof; OAr is aroxy; B is OCOR' or OAr; R' is hydrogen or a monovalent organic group having from 1 to 100 carbon atoms; $x+y+z$ equal 4; $p+q$ equal 3; $x$, $z$ and $q$ may be 1, 2 or 3; and $y$ and $p$ may be 0, 1 or 2.

17. The composition of matter of claim 16 wherein A is a sulfonic or sulfinic group having the formulas —OSO$_2$R'' and —OSOR'', respectively; and wherein R'' is a phenyl, a substituted phenyl or an alkaryl group having 5 to 24 carbon atoms in the alkyl chain, R is an alkyl group having from 1 to 6 carbon atoms, and z equals 1.

18. The composition of matter of claim 17 wherein R'' is an aminophenyl group and R is an isopropyl group.

19. The composition of matter of claim 17 wherein R'' is a dodecylphenyl group and R is an isopropyl group.

20. The composition of matter of claim 16 wherein the organo-titanate compound is of the formula I type; and wherein A is a phosphate group having the formula (R''O)$_2$P(O)- and R'' has from 6 to 24 carbon atoms, R is an alkyl group having from 1 to 6 carbon atoms, and z equals 1.

21. The composition of matter of claim 20 wherein R'' is an octyl group and R is an isopropyl group.

22. The composition of matter of claim 16 wherein the organo-titanate compound is of the formula I type; wherein A is a pyrophosphate group having the formula (R''O)$_2$P(O)OP(OH)O-; and wherein R'' is an alkyl group having up to 12 carbon atoms, R is an alkyl group having 1 to 6 carbon atoms, and z equals 1.

23. The composition of matter of claim 22 wherein R'' is an octyl group and R is an isopropyl group.

24. The composition of matter of claim 16 wherein the organo-titanate compound is of the formula II type; and wherein Ar is an alkyl-substituted derivative of a phenyl or a naphthyl group and R is an alkyl group having 1 to 6 carbon atoms.

25. The composition of matter of claim 16 wherein the organo-titanate compound is of the formula II type and wherein Ar is a cumylphenyl group and q equals 3.

26. The composition of matter of claim 16 wherein the inorganic material is selected from the group consisting of metals, metal oxides, carbon black, sulfur, talc, calcium carbonate, silica and clay.

27. The composition of matter of claim 16 wherein the metal oxide is zinc oxide, magnesium oxide, titanium oxide, yellow iron oxide, calcium oxide, and lead oxide.

28. A filled polymeric composition which comprises a polymeric material containing a compound having the formula:

(RO)$_z$Ti(A)$_x$(B)$_y$     (I)

(RO)Ti(OCOR')$_p$(OAr)$_q$     (II)

wherein R is a monovalent alkyl, alkenyl, alkynyl, or aralkyl group having from 1 to 30 carbon atoms or substituted derivatives thereof; A is a thioaroxy, sulfonic, sulfinic, diester pyrophosphate, diester phosphate, or a substituted derivative thereof; OAr is aroxy; B is OCOR'' or OAr; R' is hydrogen or a monovalent organic group having from 1 to 100 carbon atoms; $x+y+z$ equal 4; $p+q$ equal 3; $x$, $z$ and $q$ may be 1, 2 or 3; and $y$ and $p$ may be 0, 1 or 2.

29. The polymeric composition of claim 28 wherein the polymer is polyvinyl chloride.

30. The polymeric composition of claim 28 wherein the polymeric material is EPDM or a styrene-butadiene rubber.

31. The polymeric composition of claim 28 wherein the polymeric material is a polyethylene.

32. The filled polymeric composition of claim 28 wherein the compound is of the formula I type; wherein A is a sulfonic or sulfinic group having the formulas —OSO$_2$R'' and —OSOR'', respectively; and wherein R'' is a phenyl, a substituted phenyl or an alkaryl group having 5 to 24 carbon atoms in the alkyl chain, R is an alkyl group having from 1 to 6 carbon atoms, and z equals 1.

33. The filled polymeric composition of claim 32 wherein R'' is an aminophenyl group and R is an isopropyl group.

34. The filled polymeric composition of claim 32 wherein R'' is a dodecylphenyl group and R is an isopropyl group.

35. The filled polymeric composition of claim 28 wherein the compound is of the formula I type; and wherein A is a phosphate group having the formula (R''O)P(O)-, R'' has from 6 to 24 carbon atoms, R is an alkyl group having from 1 to 6 carbon atoms, and z equals 1.

36. The filled polymeric composition of claim 35 wherein R'' is an octyl group and R is an isopropyl group.

37. The filled polymeric composition of claim 28 wherein the compound is of the formula I type; wherein A is a pyrophosphate group having the formula (R''O)$_2$P(O)OP(OH)O—; and wherein R'' is an alkyl group having up to 12 carbon atoms, R is an alky group having 1 to 6 carbon atoms, and z equals 1.

38. The filled polymeric composition of claim 37 wherein R'' is an octyl group and R is an isopropyl group.

39. The filled polymeric composition of claim 28 wherein the compound is of the formula II type; and wherein Ar is an alkyl-substituted derivative of a phenyl or a naphthyl group and R is an alkyl group having 1 to 6 carbon atoms.

40. The filled polymeric composition of claim 39 wherein Ar is a cumylphenyl group and q equals 3.

41. A filled polyester resin which comprises a polyester resin containing an inorganic filler which has been pretreated with an organo-titanate compound having the formula:

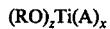
(RO)$_z$Ti(A)$_x$ wherein R is an alkyl group having 1 to 6 carbon atoms, A is a diester phosphate or a sulfonic group, and x and z are 1, 2 and 3; the total of x and z being 4.

42. The filled polyester resin of claim 41 wherein the filler is calcium carbonate.

43. A filled polyvinyl chloride resin which comprises a polyvinyl chloride containing an organo-titanate compound having the formula:

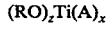
(RO)$_z$Ti(A)$_x$ wherein R is an alkyl group having 1 to 6 carbon atoms, A is a diester phosphate or a diester pyrophosphate group, and x and z are 1, 2 or 3; the total of x and z being 4.

44. The polyvinyl chloride resin of claim 43 wherein the filler is clacium carbonate.

45. The polyvinyl chloride resin of claim 43 wherein the organo-titanate compound is isopropyl tri(dioctylphosphato)titanate or isopropyl tri(dioctylpyrophosphato)-titanate.

46. A filler composition which comprises clay, the surface of which has been treated with isopropyl tri(dioctylphosphato)titanate or isopropyl tri(dioctylpyrophosphato)titanate.

47. The filler composition which comprises talc, the surface of which has been treated with isopropyl tri(dioctylphosphato)titanate or isopropyl tri(dioctylpyrophosphato)titanate.

* * * * *